(12) United States Patent
Arzoumanidis et al.

(10) Patent No.: US 8,893,398 B2
(45) Date of Patent: Nov. 25, 2014

(54) EXTENSOMETER ASSEMBLY FOR USE IN MATERIAL TESTING SYSTEMS

(75) Inventors: G. Alexis Arzoumanidis, Glenview, IL (US); Charles Meade Spellman, Chicago, IL (US); Vishaal B. Verma, Evanston, IL (US)

(73) Assignee: Psylotech, Evanston, IL (US)

( * ) Notice: Subject to any disclaimer, the term of this patent is extended or adjusted under 35 U.S.C. 154(b) by 219 days.

(21) Appl. No.: 13/620,211

(22) Filed: Sep. 14, 2012

(65) Prior Publication Data

US 2013/0061486 A1    Mar. 14, 2013

Related U.S. Application Data

(60) Provisional application No. 61/534,838, filed on Sep. 14, 2011.

(51) Int. Cl.
   *G01B 5/30* (2006.01)
   *G01B 7/16* (2006.01)
   *G01N 3/02* (2006.01)

(52) U.S. Cl.
   CPC ... *G01N 3/02* (2013.01); *G01B 5/30* (2013.01)
   USPC .......................................................... 33/790

(58) Field of Classification Search
   USPC ................................... 33/790, 787, 788, 789
   See application file for complete search history.

(56) References Cited

U.S. PATENT DOCUMENTS

| | | | | |
|---|---|---|---|---|
| 2,588,630 A * | 3/1952 | Jackman | ............. | 33/790 |
| 2,663,085 A * | 12/1953 | Ruge | ............. | 33/788 |
| 3,514,864 A * | 6/1970 | Cayocca et al. | ............. | 33/787 |
| 3,789,508 A * | 2/1974 | Meline | ............. | 33/788 |
| 4,491,021 A * | 1/1985 | Meline | ............. | 73/767 |
| 4,507,871 A * | 4/1985 | Meyer et al. | ............. | 33/790 |
| 4,831,738 A * | 5/1989 | Meline et al. | ............. | 33/790 |
| 4,831,882 A * | 5/1989 | Meline et al. | ............. | 73/826 |
| 4,939,445 A * | 7/1990 | Meline et al. | ............. | 324/663 |
| 5,119,569 A * | 6/1992 | Meline | ............. | 33/790 |
| 5,123,175 A * | 6/1992 | van der Kuur | ............. | 33/789 |
| 5,623,768 A * | 4/1997 | Menzer et al. | ............. | 33/787 |
| 6,907,677 B1 * | 6/2005 | Hartman | ............. | 33/787 |

* cited by examiner

*Primary Examiner* — Christopher Fulton
(74) *Attorney, Agent, or Firm* — The Watson I.P Group, PLC; Jovan N. Jovanovic; Vladan M. Vasiljevic (57) ABSTRACT

An extensometer assembly for use in association with a material testing system. The extensometer assembly has a pair of extensometers each of which includes a first arm and a second arm. The arms are pivotally coupled together through a connector, such as a flexure bearing. The extensometers may be positioned on opposing sides of a specimen to be tested. A pair of clips extending between opposing first arms and opposing second arms, respectively, retains the extensometers engaged to the specimen on opposing sides of the specimen.

18 Claims, 10 Drawing Sheets

Figure 12 ously configured to engage a specimen. A first sensor is configured to sense relative pivoting of the first arm and the second arm.

EXTENSOMETER ASSEMBLY FOR USE IN MATERIAL TESTING SYSTEMS

CROSS-REFERENCE TO RELATED APPLICATION

This application claims priority from U.S. Prov. Pat. App. Ser. No. 61/534,868 filed Sep. 14, 2011, entitled, Sensing Equipment, Software And Methods Associated Therewith, the entire specification of which is hereby incorporated by reference in its entirety.

BACKGROUND OF THE DISCLOSURE

1. Field of the Disclosure

The disclosure relates in general to material testing systems, and more particularly, to an extensometer assembly for use in association with material testing systems, and in particular, polymer material testing systems.

2. Background Art

The use of extensometers is well known in the art. Generally extensometers are utilized in association with materials testing systems. Typically, a single extensometer or pairs of extensometers are positioned about a test specimen. When a load is applied to the test specimen, the extensometers measure strain and/or displacement, that is, a physical change in the dimension of the specimen about the location of the extensometer. Generally, such measurements are measured by the sensor and then recorded or logged and processed by processing equipment (such as computers).

With testing of polymer materials, additional considerations are presented. Specifically, as polymers are generally much lighter than metals, the weight of the extensometer becomes a more critical factor. While it is important to address the weight and mass effect of the extensometer, the extensometer requires compliance, as stiffness of the extensometer would undesirably affect the accuracy of the extensometer. Additionally, it is important that the relative movement of the displacement arms occur in a frictionless environment so as not to introduce additional variables. Furthermore, it is often difficult to position sensing equipment in a position that allows for displacement of the arms without affecting the specimen.

Additionally, it is often the case that different extensometers must be utilized when obtaining displacement measurements in the direction of force application and in a direction perpendicular to the force application. Often the manner in which opposing extensometers are coupled limits the use of the extensometer to either one type of measurement or another type of measurement.

SUMMARY OF THE DISCLOSURE

The disclosure is directed to an extensometer for use in association with an extensometer assembly. The extensometer includes a first arm, a second arm, a flexure bearing and at least one sensor. The first arm includes a proximal end and a distal end. A bearing bore is positioned at the proximal end thereof with a specimen contact assembly positioned at the distal end thereof. The second arm includes a proximal end and a distal end. A bearing bore is positioned at the proximal end thereof and a specimen contact assembly is positioned at the distal end thereof. A flexure bearing extends between the first arm and the second arm at the proximal end of each of the first arm and the second arm and into the bearing bore positioned at the proximal ends of each of the first and second arms. In such a configuration, the first and second arms are positioned in a side by side orientation. The at least one sensor assembly has a component coupled to each of the first arm and the second arm. The at least one sensor configured to sense relative pivoting of the first arm and the second arm relative to each other.

In a preferred embodiment, the specimen contact assembly of at least one of the first arm and the second arm comprises an outer clamp, an inner clamp and a specimen contact member. The outer clamp component is positioned at the distal end of the first arm. The inner clamp component is configured to engage with the outer clamp component. The specimen contact member is configured to extend between the outer clamp component and the inner clamp component, to, in turn, sandwich the specimen contact member therebetween.

In a preferred embodiment, the specimen contact member extends from the distal end of the respective one of the first arm and second arm substantially perpendicular to the specimen.

In another preferred embodiment, the specimen contact member extends from the distal end of the respective one of the first arm and second arm substantially oblique to the specimen. The specimen contact member comprises a generally rectangular cross-sectional configuration, to, in turn, facilitate contact with a specimen along an edge of the specimen contact member.

In another preferred embodiment, the flexure bearing comprises a cylindrical member which is encased within the bearing bore of each of the first arm and second arm.

In another preferred embodiment, the sensor subassembly further comprises a first sensor winding fixedly coupled to the first arm between the first and second end thereof, and a second sensor winding fixedly coupled to the second arm between the first and second end thereof. A first core is coupled to the second arm so as to move relative to the first sensor winding upon relative pivoting between the first arm and the second arm. A second core is coupled to the first arm so as to move relative to the second sensor winding upon relative pivoting between the first arm and second arm.

In another preferred embodiment, relative pivoting movement of the first arm relative to the second arm directs one of the first core and second core further into the respective first sensor winding and second sensor winding. At the same time the relative pivoting movement directs the other of the first core and the second core further out of the respective other of the first sensor winding and second sensor winding.

In a preferred embodiment, the movement of the first core relative to the first winding is inversely related to the second core relative to the second winding.

In a preferred embodiment, the first core and the second core extends from the top surface of each of the first arm and the second arm.

In another preferred embodiment, each of the first arm and the second arm is formed from a single monolithic metal member.

Preferably, each of the first sensor windings and the second sensor windings extend into a respective bore extending into the first arm and the second arm between the proximal and distal ends thereof.

In another embodiment, the first sensor winding and the second sensor winding are substantially identical in configuration.

In another aspect of the disclosure, the disclosure comprises an extensometer assembly which comprises a first extensometer, a second extensometer and an attachment assembly. The first extensometer is positionable on a first side of a specimen and includes a first arm and a second arm pivotally coupled to each other at a proximal end, and engageable with a specimen at a distal end thereof about a specimen contact member. The second extensometer is positionable on a second side of a specimen, which is opposite the first side of a specimen. The second extensometer comprises a first arm and a second arm pivotally coupled to each other at a proximal end. The second extensometer is engageable with a specimen at a distal end thereof about a specimen contact member. The attachment assembly is configured to attach the first extensometer to the second extensometer.

The attachment assembly comprises a first clip and a second clip. The first clip has a first end coupled to the distal end of the first arm of the first extensometer and a second end coupled to the distal end of the first arm of the second extensometer. The first clip extends one of substantially oblique and substantially parallel to the specimen contact member, to, in turn, facilitate attachment of the extensometer assembly in an orientation wherein the specimen contact member is substantially parallel to the direction of a force that is to be applied to the specimen and in an orientation wherein the specimen contact member is substantially perpendicular to the direction of a force that is to be applied to the specimen.

Similarly, the second clip has a first end coupled to the distal end of the second arm of the first extensometer and a second end coupled to the distal end of the second arm of the second extensometer. The first clip extends one of substantially oblique and substantially parallel to the specimen contact member, to, in turn, facilitate attachment of the extensometer assembly in an orientation wherein the specimen contact member is substantially parallel to the direction of a force that is to be applied to the specimen and in an orientation wherein the specimen contact member is substantially perpendicular to the direction of a force that is to be applied to the specimen.

In a preferred embodiment, each of the first end and the second end of the first clip include a valley and the top surface of the first arm of each of the first extensometer and the second extensometer each include an opening disposed on a respective top surface thereof. The respective valley of each of the first end and second end engages a respective opening of the first arm of the respective first and second extensometers, to, in turn, releasably engage the same.

In another preferred embodiment, each of the first end and the second end of the second clip include a valley and the top surface of the second arm of each of the first extensometer and the second extensometer each include an opening disposed on a respective top surface thereof. The respective valley of each of the first end and second end engages a respective opening of the first arm of the respective first and second extensometers, to, in turn, releasably engage the same.

In another preferred embodiment, the opening is disposed on the respective top surface of each of the first arms of each of the first and second extensometers which are disposed at an angle that substantially corresponds to that of the valley at the first end and second end of the first clip. In such a configuration, a portion of the distal end engages a surface of the opening, to, in turn, provide a surface of contact between the first and second end.

In a preferred embodiment, each of the extensometers are tuned to a resonant frequency that is between 10 Hz and 100 Hz. In one such embodiment, each of the extensometers are tuned to a resonant frequency that is above 50 Hz.

BRIEF DESCRIPTION OF THE DRAWINGS

The disclosure will now be described with reference to the drawings wherein.

DETAILED DESCRIPTION OF THE DISCLOSURE

While this disclosure is susceptible of embodiment in many different forms, there is shown in the drawings and described herein in detail a specific embodiment with the understanding that the present disclosure is to be considered as an exemplification and is not intended to be limited to the embodiment illustrated.

It will be understood that like or analogous elements and/or components, referred to herein, may be identified throughout the drawings by like reference characters. In addition, it will be understood that the drawings are merely schematic representations of the invention, and some of the components may have been distorted from actual scale for purposes of pictorial clarity.

Figure 1:
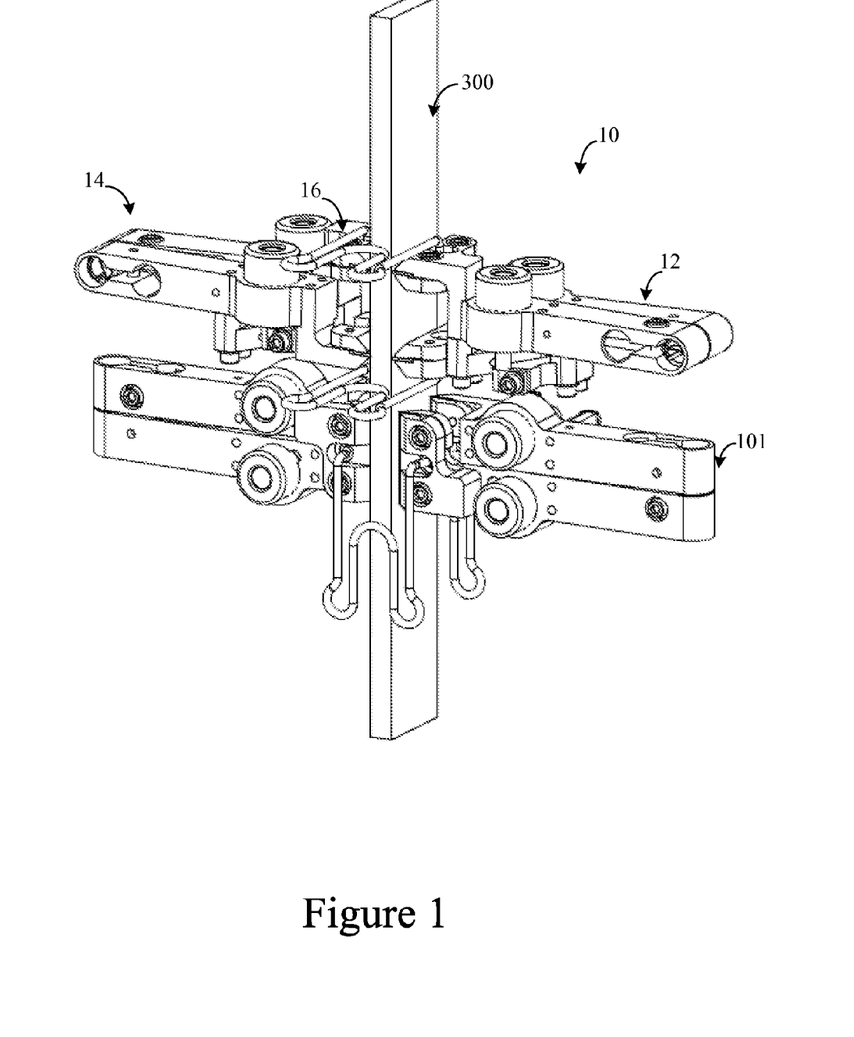
FIG. 1 of the drawings is a perspective view of a pair of extensometer assemblies of the present disclosure, positioned on a specimen, which can be loaded onto a material test frame (not shown)

Referring now to the drawings and in particular to FIG. 1, extensometer assembly is shown generally at 10, and a second extensometer assembly shown as 10'. The extensometer is particularly useful for use in materials testing of polymers, however, its use is not limited thereto, and uses in association with other testing devices, other materials and other environments is likewise contemplated.

The extensometer assembly 10 is shown in FIG. 1 as comprising a pair of extensometers, namely first extensometer 12 and second extensometer 14, as well as attachment assembly 16. The extensometer assembly, as is shown in FIG. 1, extends around the test specimen 300, and in particular, the pair of extensometers are positioned on either side of the specimen and coupled together through attachment assembly 16. It will be understood that such a test specimen 300 can be coupled at either end to grips at least one of which is coupled to a load cell or the like to facilitate the separation of the grips and, in turn, the application of a tensile load onto the specimen.

Figure 2:
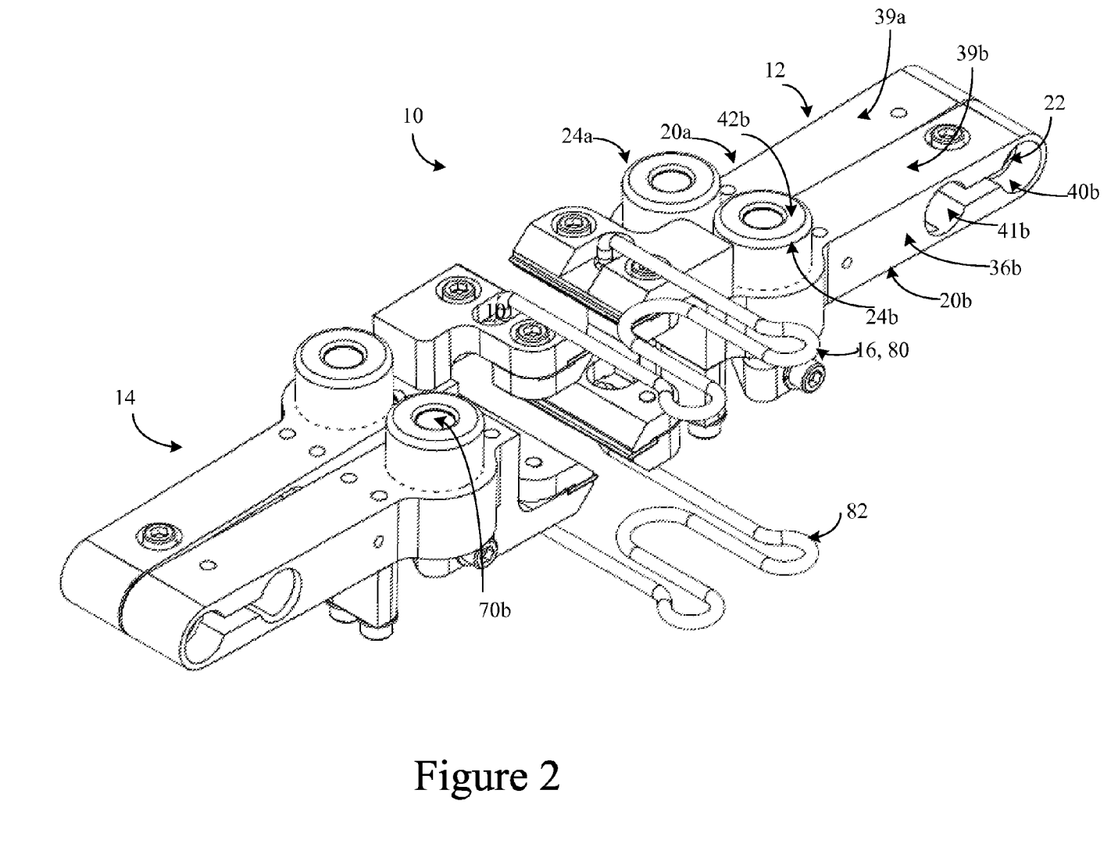
FIG. 2 of the drawings is a perspective view of an extensometer assembly of the present disclosure.
Figure 3:
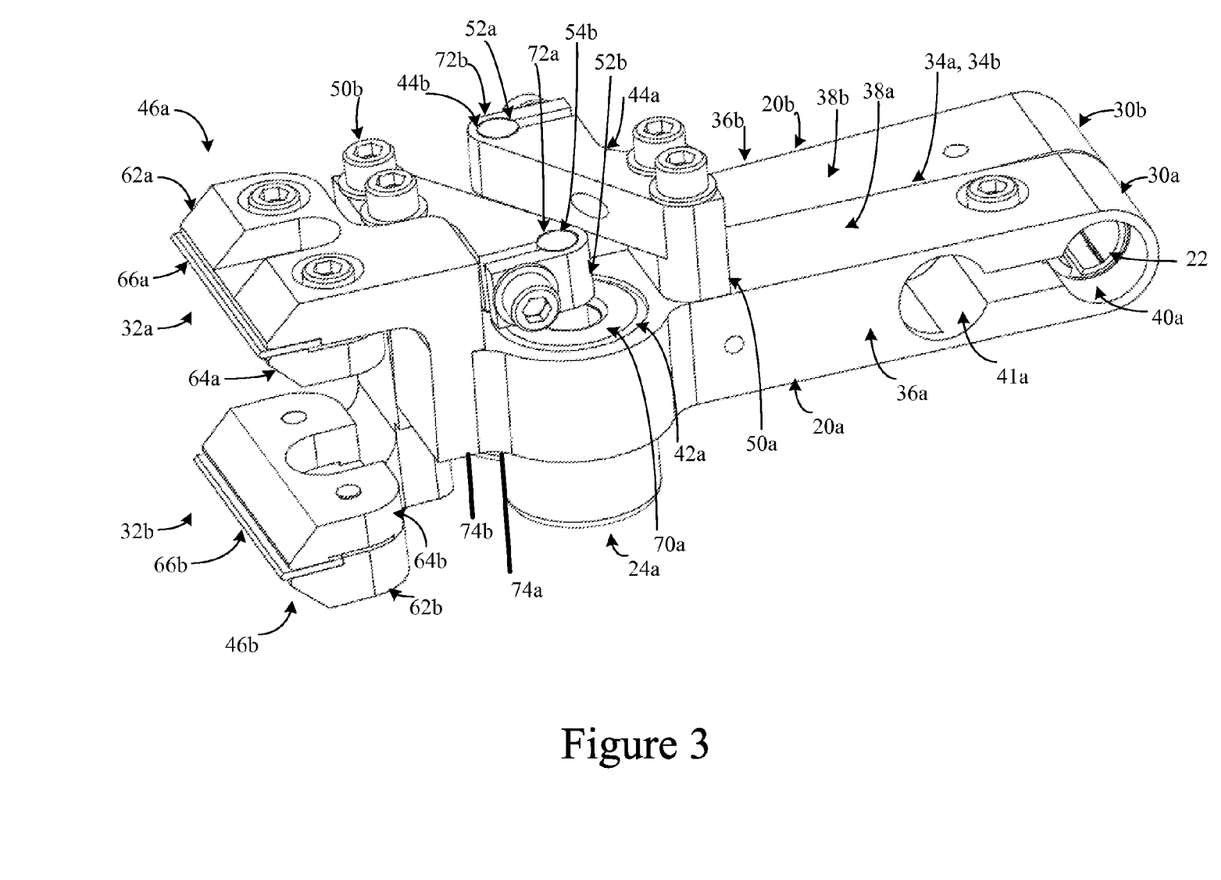
FIG. 3 of the drawings is a perspective view of an extensometer of the present disclosure.

In the embodiment shown, the first extensometer 12 will be disclosed with the understanding that the second extensometer is a substantial mirror image thereof, and/or substantially identical thereto. With reference to FIGS. 2 and 3, collectively, the first extensometer 12 includes first arm 20*a*, second arm 20*b*, flexure bearing 22, first sensor subassembly 24*a* and second sensor subassembly 24*b*. The first arm 20*a* includes proximal end 30*a*, distal end 32*a*, inner side 34*a*, outer side 36*a*, top surface 38*a* and bottom surface 39*a*. While not required, much of the first arm 20*a* comprises a single monolithic component which can be integrally cast and machined from a single piece of metal, preferably, an aluminum material. Of course, other materials are likewise contemplated, including, but not limited to various metals and alloys thereof. Additionally, it is contemplated that certain composites or polymers (especially reinforced polymers) may be utilized. The disclosure is not limited to any particular material, or any particular construction. In the embodiment shown, the total weight of the fully assembled extensometer is on the order of 11 grams.

The first arm 20*a* further includes bearing bore 40*a* extending from the inner side 34*a* to the outer side 36*a* at the proximal end 30*a*. The bearing bore 40*a* is associated with a clamping assembly 41*a*. Between the proximal and distal ends, a sensor winding mount bore 42*a* is positioned so as to extend from top surface 38*a* through to bottom surface 39*a*. Generally, the bore is configured to receive the first sensor windings 70*a* of the first sensor subassembly 24*a*, as will be described below.

A core mount arm 44*a* extends from the top surface 38*a* of the first arm 20*a* and includes first end 50*a* and second end 52*a*. A core bore 54*a* is positioned at the second end 52*a* and corresponds to the second sensor windings 70*b* of the second sensor subassembly 24*b* positioned on the second arm 20*b*. The core mount arm may be integrally formed with the core mount arm 44*a*, or may be a separate component that is coupled thereto, such as, with fasteners and the like.

At the distal end 32*a* of the first arm 20*a* the specimen contact assembly 46*a* is positioned and is formed of an outer clamp component 62*a*, inner clamp component 64*a* and specimen contact component 66*a*. The outer clamp component is integrally formed with the first arm 20*a*, and has a width that substantially extends across the second arm 20*b*, such that the top surface 38*a* has a substantially L-like configuration. Additionally, the outer clamp component is offset from the remainder of the first arm 20*a*, such that the distal end has a stepped appearance when viewing the outer side 36*a*. The inner clamp 64*a* is coupled to the underside of the outer clamp component, so as to capture the specimen contact member therebetween. The specimen contact member includes a sharp edge which can clamp against the specimen 300 without allowing for slipping and the like. Typically, the specimen contact member includes either two contact prongs that are spaced apart from each other, or a single contact prong, so that between the first and second arms of each of the extensometers 12, 14, two prongs are positioned on the opposite side of a single contact prong, so that at any given place of contact between opposing extensometers, a total of three contact prongs contact the specimen, one on one side and two on the other side, where the one straddles between the two. In other embodiments, the prongs may also be mirror images of each other about the specimen. In still other embodiments, the specimen contact member may comprise a substantially uniform edge without any protrusions or contact prongs.

In the embodiment shown, the outer clamp component 62*a* and the inner clamp component 64*a* are held together with screws. It will be understood that by tightening the screws, the specimen contact member is sandwiched therebetween. It will also be understood that the specimen contact member includes openings that are elongated slots, and even slots that extend to an edge of the specimen contact member so as to allow a degree of movement of the specimen contact member when positioned between the clamp components. Of course, in other embodiments, the openings on the specimen contact member through which the tightening screws extend may be sized to snugly receive the tightening screws, so as to preclude any relative movement and adjustment.

With continued reference to FIGS. 2 and 3, the second arm 20*b*, as set forth above comprises a substantial corresponding structure to the first arm 20*a* and further includes bearing bore 40*b* extending from the inner side 34*b* to the outer side 36*b* at the proximal end 30*b*. The bearing bore 40*b* is associated with a clamping assembly 41*b*. Between the proximal and distal ends, a sensor winding mount bore 42*b* is positioned so as to extend from top surface 38*b* through to bottom surface 39*b*. Generally, the bore is configured to receive the first sensor windings 70*b* of the second sensor subassembly 24*b*, as will be described below.

A core mount arm 44*b* extends from the top surface 38*b* of the second arm 20*b* and includes first end 50*b* and second end 52*b*. A core bore 54*b* is positioned at the second end 52*b* and corresponds to the first sensor windings 70*a* of the first sensor subassembly 24*a* positioned on the first arm 20*a*. The core mount arm may be integrally formed with the core mount arm 44*b*, or may be a separate component that is coupled thereto, such as, with fasteners and the like. Interestingly, both of the core mounting arms 44*a*, 44*b* extend from the top surfaces 38*a*, 38*b* (or in other embodiments the bottom surfaces 39*a*, 39*b*) of both of the arms 20*a*, 20*b*, and are coupled to a core that translates through the windings of the sensor positioned on the other arm. In turn, as the two arms move in opposite directions, as the arms radially spread apart from each other (wherein the distal ends extend further away from each other), the core of the first sensor which is coupled to the second arm retreats from the first sensor winding, while the core of the second sensor which is coupled to the first arm extends further into the second sensor windings.

At the distal end 32*b* of the second arm 20*b* the specimen contact assembly 46*b* is positioned and is formed of an outer clamp component 62*b*, inner clamp component 64*b* and specimen contact component 66*b*. The outer clamp component is integrally formed with the second arm 20*b*, and has a width that substantially extends across the first arm 20*a*, such that the top surface 38*b* has a substantially L-like configuration. Additionally, the outer clamp component is offset from the remainder of the second arm 20*b*, such that the distal end has a stepped appearance when viewing the outer side 36*b*. The inner clamp 64*b* is coupled to the underside of the outer clamp component, so as to capture the specimen contact member therebetween. The specimen contact member includes a sharp edge which can clamp against the specimen 300 without allowing for slipping and the like. As explained above, the specimen contact member includes either two contact prongs that are spaced apart from each other, or a single contact prong. The specimen contact assembly 46*a* of the first arm 20*a* and the specimen contact assembly 46*b* of the second arm assembly 20*b* are such that they are substantial mirror images of each other and generally spaced apart parallel to each other, and generally rotate toward and away from each other so that the parallel relationship of the specimen contact member is maintained. In other embodiments, the specimen contact member may comprise a substantially uniform edge without any protrusions or contact prongs.

In the embodiment shown, the outer clamp component 62b and the inner clamp component 64b are held together with screws. Just as with the first arm 20a, it will be understood that by tightening the screws, the specimen contact member of the second arm is sandwiched therebetween.

Figures 4, 5:
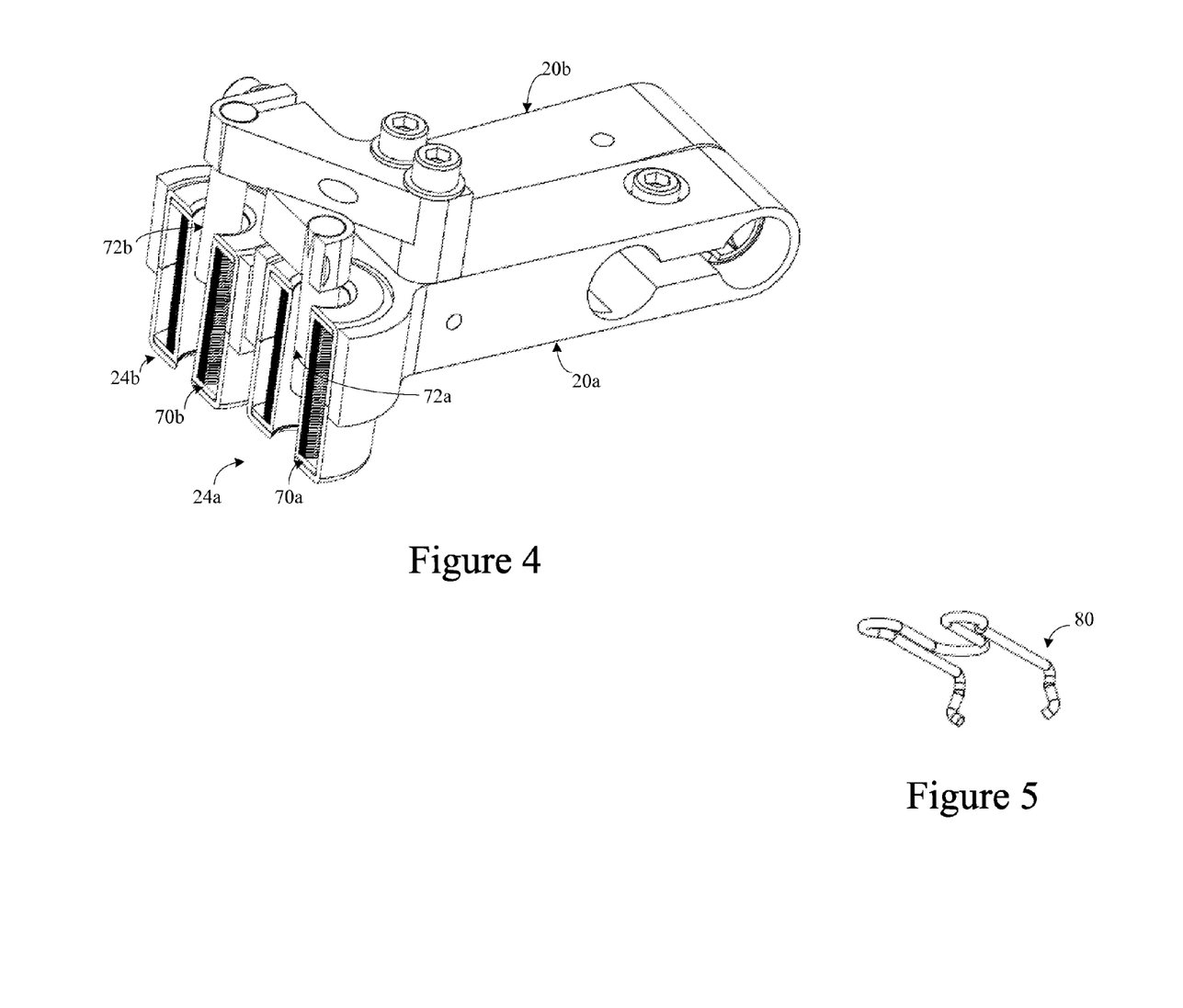
FIG. 4 of the drawings is a perspective cross-sectional view of an extensometer of the present disclosure, taken generally about line 4-4 of FIG. 3.
FIG. 5 of the drawings is a cross-sectional view of a flexure bearing of the type utilized in association with the present disclosure.
Figure 6:
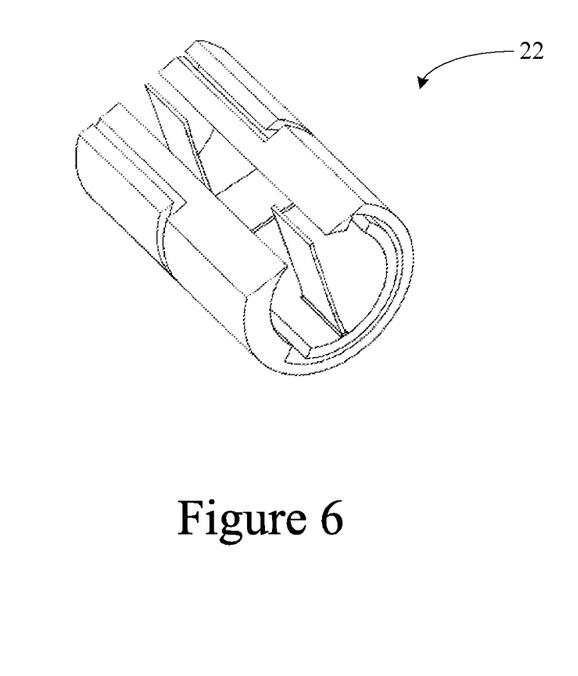
FIG. 6 of the drawings is a cross-sectional view of a flexure bearing of the type utilized in association with the present disclosure.
Figure 8:
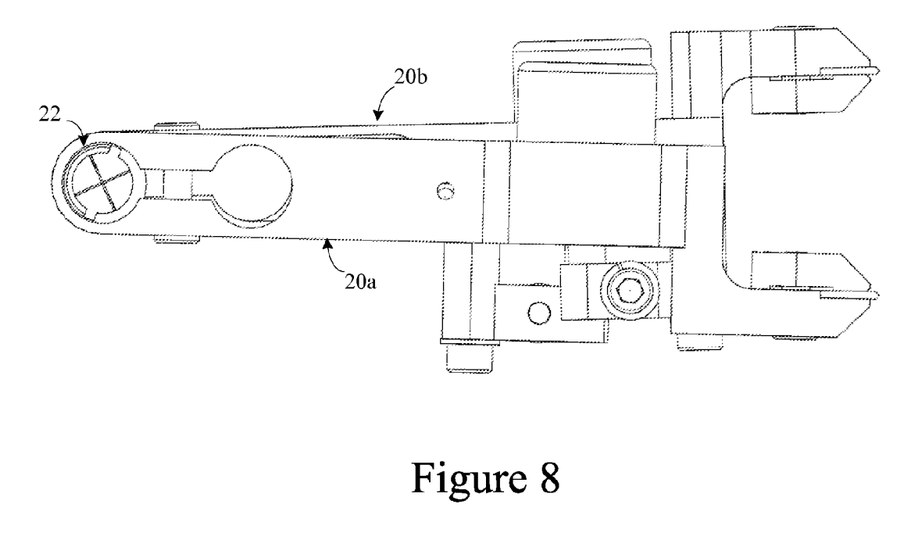
FIG. 8 of the drawings is a side elevational view of the extensometer of the present disclosure.

The first arm 20a and the second arm 20b are positioned in a side by side orientation with the inner sides 34a, 34b generally abutting each other (typically in a slightly spaced apart orientation). In such a configuration, the specimen contact assemblies overlie each other and are spaced apart from each other. The first arm 20a and the second arm 20b are rotatably coupled to each other about the proximal end 30a through a rotatable pivot, such as a flexure bearing 22. With reference to FIGS. 5, 6 and 8, the flexure bearing 22 has components that are bound and move with each one of the first arm 20a and the second arm 20b, and other portions which are allowed to move relative to each of the components. In turn, such a configuration allows for a frictionless pivotable junction between the two components, allowing one arm to pivot relative to the other arm through a certain distance (typically, a flexure bearing has internal stops that limit further rotative movement), however, generally, such limitations are typically outside of the desired operating range of the extensometer. Of course, other pivotable connecting members are likewise contemplated for use, including, but not limited to different bearing structures and hinges. Advantageously, a flexure bearing, especially one that is as compact as the flexure bearing shown residing within the bearing bores 40a, 40b, is of limited size and does not introduce frictional issues and frictional losses into the system.

The first sensor subassembly 24a is shown in FIGS. 2 and 4 as comprising first sensor winding 70a, and first sensor core 72a. The first sensor winding is positioned to extend through the first sensor mount bore 42a, and includes a lead coming from either end thereof. The first sensor core 72a extends from the core mount arm 44b of the second arm 20b. As such, relative movement of the first arm and the second arm directs the core further into or further out of the first sensor winding 70a, which, in turn, changes the relative voltage across the windings.

The second sensor subassembly 24b is shown in FIGS. 2, 3 and 4 as comprising second sensor winding 70b, and second sensor core 72b. The second sensor winding is positioned to extend through the second sensor mount bore 42b, and includes a lead coming from either end thereof. The second sensor core 72b extends from the core mount arm 44a of the first arm 20a. As such, relative movement of the first arm and the second arm directs the core further into or further out of the second sensor winding 70b. It will be understood that by positioning the core mount arms on the same side of the arms, and coupling a core that interfaces with the sensor windings of the opposing arm, relative movement by one of the cores is met with an equal and opposite movement by the other of the cores. The two cores combine to form an inductive voltage divider, which is one half of a Wheatstone bridge. Advantageously, by positioning two smaller windings on each of the arms with two separate cores, instead of a core on one arm and a winding on the other arm, substantially shorter cores can be utilized. In turn, as the arms move in an arc relative to each other, there is likelihood of interference between the core and the surrounding winding. Additionally, the cores can form the first half of the bridge which can be utilized in other novel manners (i.e., cancelling of signals, obtaining moments and the like).

Figure 7:
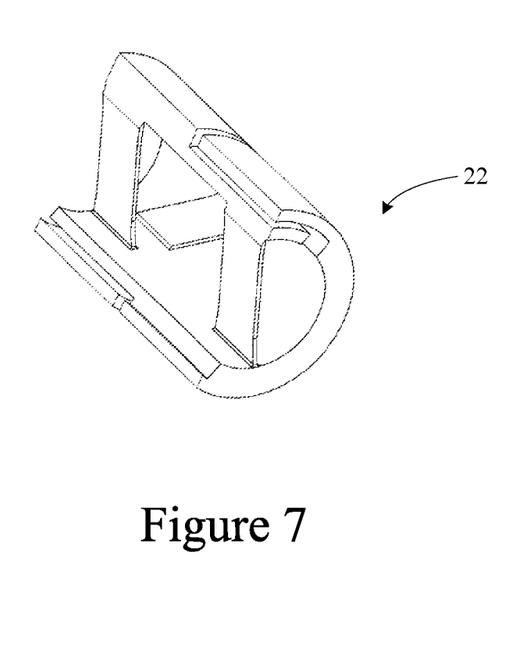
FIG. 7 of the drawings is a perspective view of the clip of the type utilized in association with the present disclosure.

It will be understood that the second extensometer is substantially identical to the first extensometer and that they are mounted on opposing sides of the specimen 300. The attachment assembly 16 couples the two extensometers to each other. With reference to FIG. 2, in the embodiment shown, the attachment assembly 16 comprises a pair of clips 80 and 82 (one such clip is shown in FIG. 7 in greater detail). First clip 80 extends from the distal end 32a of the first arm 20a to a corresponding distal end of the first arm of the extensometer 14 positioned on the opposite side of specimen 300. Similarly, second clip 82 extends from distal end 32b of the second arm 20b to a corresponding distal end of the second arm of extensometer 14 positioned on the opposite side of specimen 300. Each of the clips includes a v-shaped distal end defining a valley. This valley engages the respective opening on the respective arm so as to maintain the respective arm in the desired orientation.

It will be understood that the clips are offset away from the top surfaces of their respective arms, and extend away from the extensometers in a generally perpendicular fashion. The material and the shape of the clips also biases the opposing extensometer arms toward each other, only enhancing the grip that the specimen contact members have on the specimen 300.

By extending the clips away from the top surfaces of the respective arms, and in a direction that is substantially off toward the outer side of one of the respective arms, the clips and extensometer are suitable for use in either a first orientation, wherein the arms of an extensometer are positioned along the specimen so that the specimen contact member is substantially perpendicular to the direction of the applied load (i.e., to measure changes in length), and a second orientation, wherein the arms of an extensometer are positioned along the specimen so that the specimen contact member is substantially parallel to the direction of the applied load (to measure changes in width). Advantageously, each of the extensometers can be identical and the same pair of extensometers and clips can be utilized in either orientation; there is no need for different extensometers or clips when a different orientation is sought.

Figure 9:
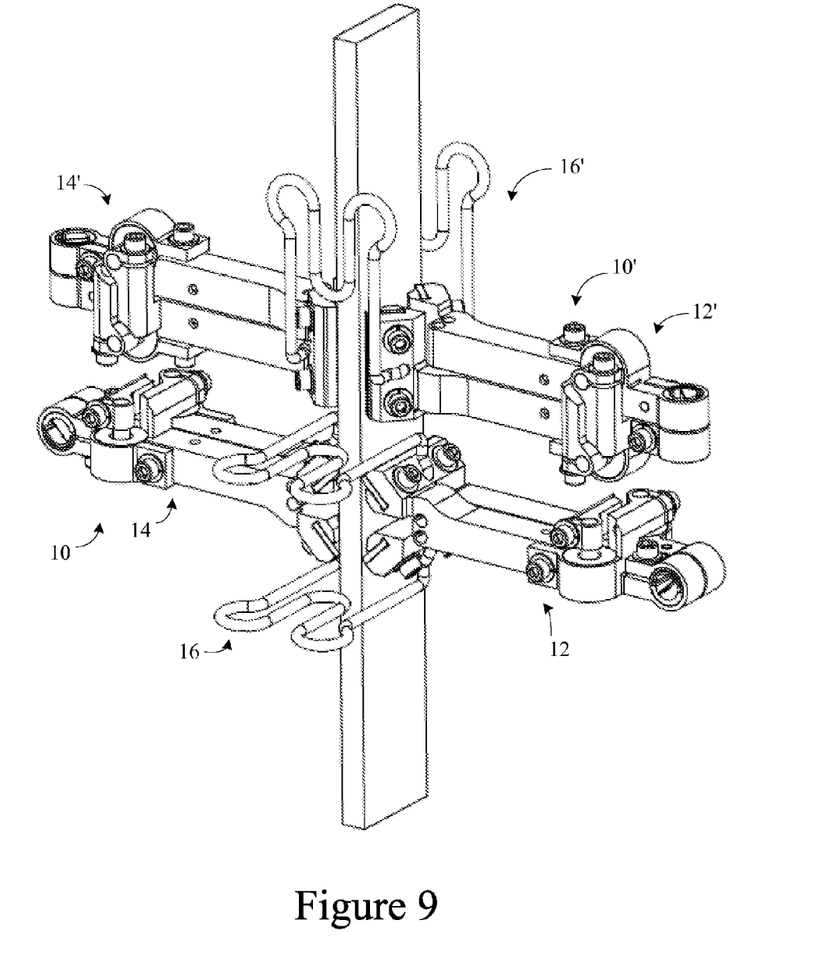
FIG. 9 of the drawings is a perspective view of a second embodiment of a pair of extensometer assemblies of the present disclosure, positioned on a specimen, which can be loaded onto a material test frame (not shown)
Figure 10:
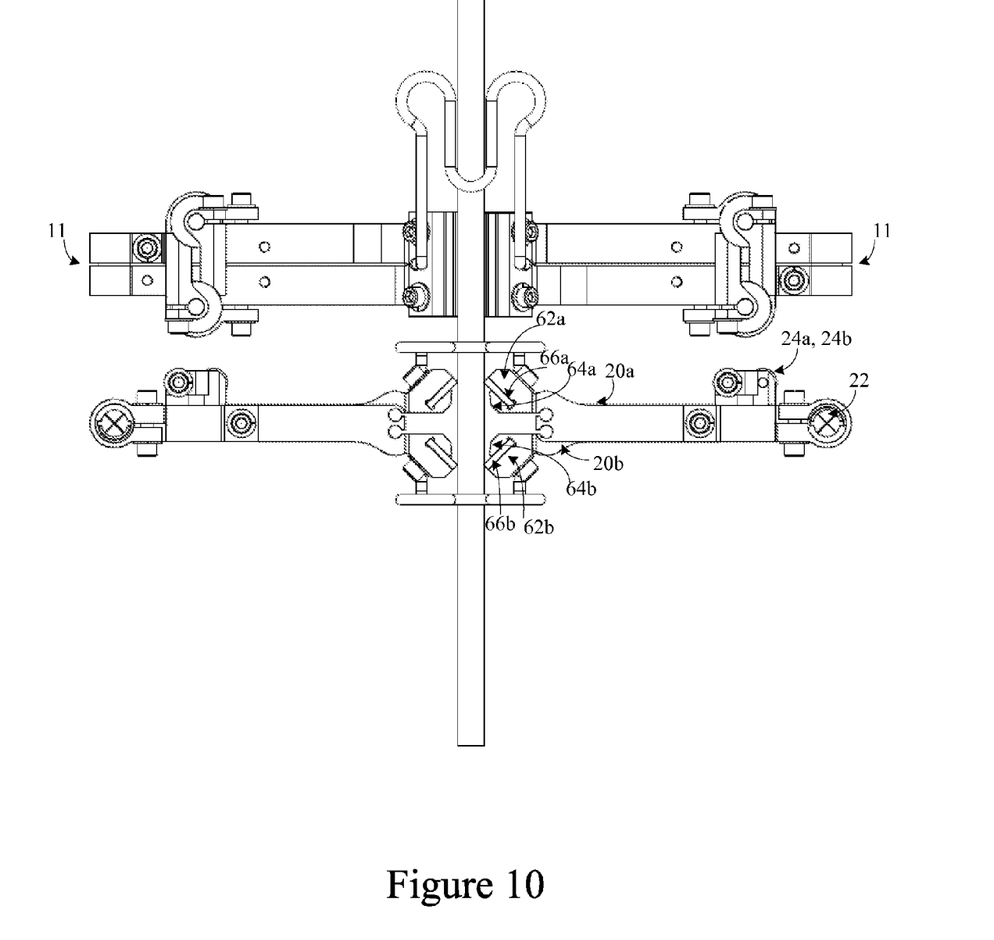
FIG. 10 of the drawings is a side elevational view of a second embodiment of the pair of extensometer assemblies of the present disclosure, positioned on a specimen, as is shown in FIG. 9.
Figure 11:
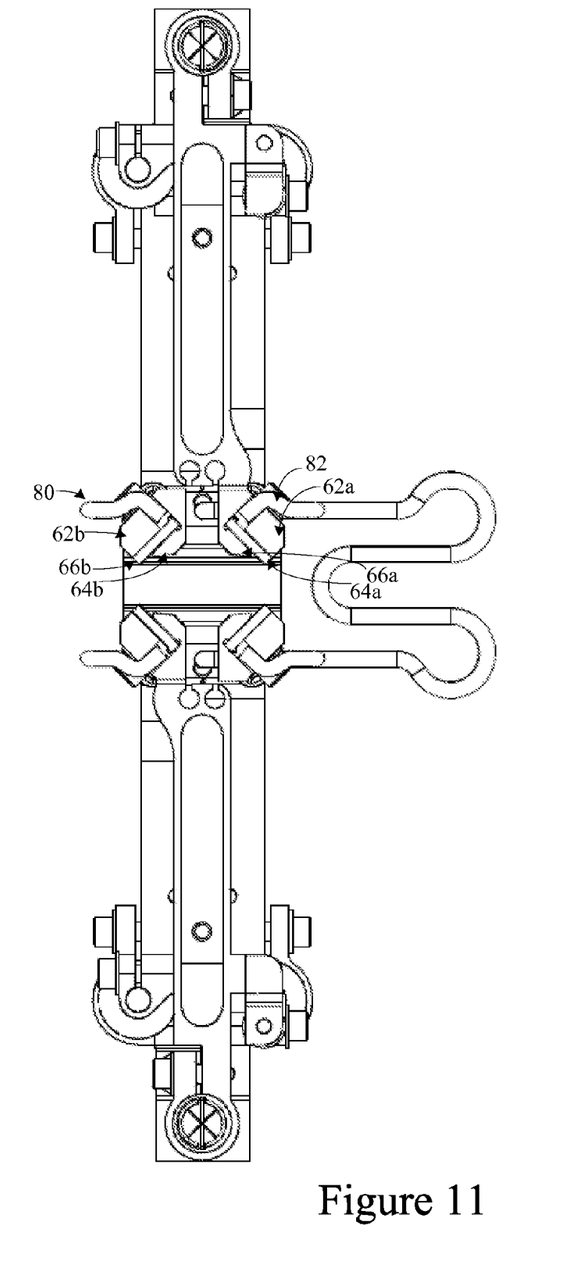
FIG. 11 of the drawings is a cross-sectional view of the second embodiment of the pair of extensometer assemblies of the present disclosure, showing, in particular, the interface between the clips and the second ends of the respective first and second arms of each of the extensometers.

In another embodiment of the extensometer, shown in FIGS. 9 through 11, the specimen contact assembly is disposed at an oblique angle relative to the respective arm. In the embodiment shown, the specimen contact assembly is angled at an angle of approximately 45°, whereas in the embodiment of FIGS. 1 through 8, the specimen contact assembly was positioned so as to be substantially parallel to the general longitudinal axis of the respective arm. There are a number of advantages to such a configuration. Among other advantages, the specimen contact member can be formed from a material having a substantially rectangular cross-sectional configuration. When positioned at 45° relative to the respective arm (and the specimen), the edge of the specimen contact member is configured to contact and engage the specimen contact member. Thus, it is not necessary to provide sharpened edges, a straight cut yields strong and sharp corners when positioned in the obliquely oriented specimen contact assembly.

Finally, as is shown in the embodiment of FIGS. 9 through 11, the sensor subassembly 24a, 24b (and in turn, the bearing bores 40a, 40b, and, the sensor mounts 42a, 42b) can be moved closer to the proximal ends of the respective arms. This allows for less clearance issues between the respective sensor cores vis-à-vis the respective sensor windings.

The embodiment of FIGS. 9 through 11 include a means by which to cancel the inertial forces. In particular, by moving the sensor subassembly 24a, 24b, and by reducing weight, through removing material and the like, the mass can be lowered, as well as the inertial moment (which is a function of the radius away from the flexure bearing). Reducing the radius, increases the resonant frequency. It has been found that at testing at a frequency of 10 Hz on the sample begins to introduce inertial effects. To cancel the effects, or to minimize the same, it has been found that through the foregoing structural changes, a cancellation of the inertial effects can be achieved. The particular extensometer shown in FIGS. 9 through 12 has a resonant frequency of 63 Hz, such that on a logarithmic scale, through much of the testing range, at least a portion of the inertial effects have been cancelled (typically, testing is done between 10 Hz and 100 Hz, and on a log scale, a majority of the data is obtained through testing below 63 Hz). Thus, the cancellation only further enhances the moment of inertia. Setting the resonant frequency as close to the upper limit is preferred, which is generally around 100 Hz, although, beneficial effects can certainly be seen above 50 Hz and even approaching 50 Hz or below.

In operation, and with reference to FIG. 1 and/or FIG. 9, the user first positions the specimen 300 in a load frame (not shown) leaving one end free. Once positioned, the user can attach the extensometer assembly 10. In the embodiment shown, the first extensometer assembly 10 is positioned so that the specimen contact members are substantially perpendicular to the force applied to the specimen 300. The two joined extensometers 12, 14 are spread apart, (which overcomes the spring force of the clips). The extensometer is then placed near the free end of the specimen and the specimen is directed through the hoop created by the extensometer and the clips. The first extensometer 12 is positioned on one side of the specimen, and the second extensometer 14 is positioned on the opposite side of the specimen, being careful to line up the opposing specimen contact members in close alignment.

The extensometers are slowly released so that they first engage the specimen, and then so that the clips provide the necessary biasing force against the specimen. Advantageously, as described above, the orientation of the clips is such that there is no interference with the specimen, and the clips extend easily around the outer sides of the specimen, straddling the specimen therebetween. More specifically, the clips extend in a direction that is not perpendicular to the specimen contact member, which would lead to interference with the specimen. Rather, in the embodiment shown, the clips extend in a direction that is parallel to the specimen contact member. In other embodiments, an oblique relationship can be maintained between the clips and the specimen contact member, with the understanding that the closer the clips are to being perpendicular to the specimen contact member, the greater likelihood that interference will result in either the orientation of the first extensometer assembly or the orientation of the second extensometer assembly.

The leads of each sensor subassembly of each arm of each extensometer are coupled to outside electronics in a desired fashion. It will be understood that the pair of extensometers form a pair of inductive voltage dividers, which is, in turn, a complete Wheatstone bridge, and the different comparisons can be made between different nodes of the bridge to achieve different measurements. It will be understood as well that such a configuration has high compliance, as certain effects are cancelled out naturally through the bridge wiring configuration.

In the same test, or in a separate test, a second extensometer assembly 10' can be positioned so that the respective specimen contact members are substantially parallel to the force applied to the specimen. The application proceeds in the same manner as disclosed above, except that, in the embodiment shown, the extensometers are positioned in an orientation that is one quarter turn different than the first extensometer assembly. Again, in such a configuration, the clips can be utilized without interfering with the specimen. In particular, inasmuch as the clips extend outwardly from the top surfaces of the respective arms, these clips extend beyond the side edges of the specimen. In either orientation, interference with the specimen is avoided.

Figure 12:
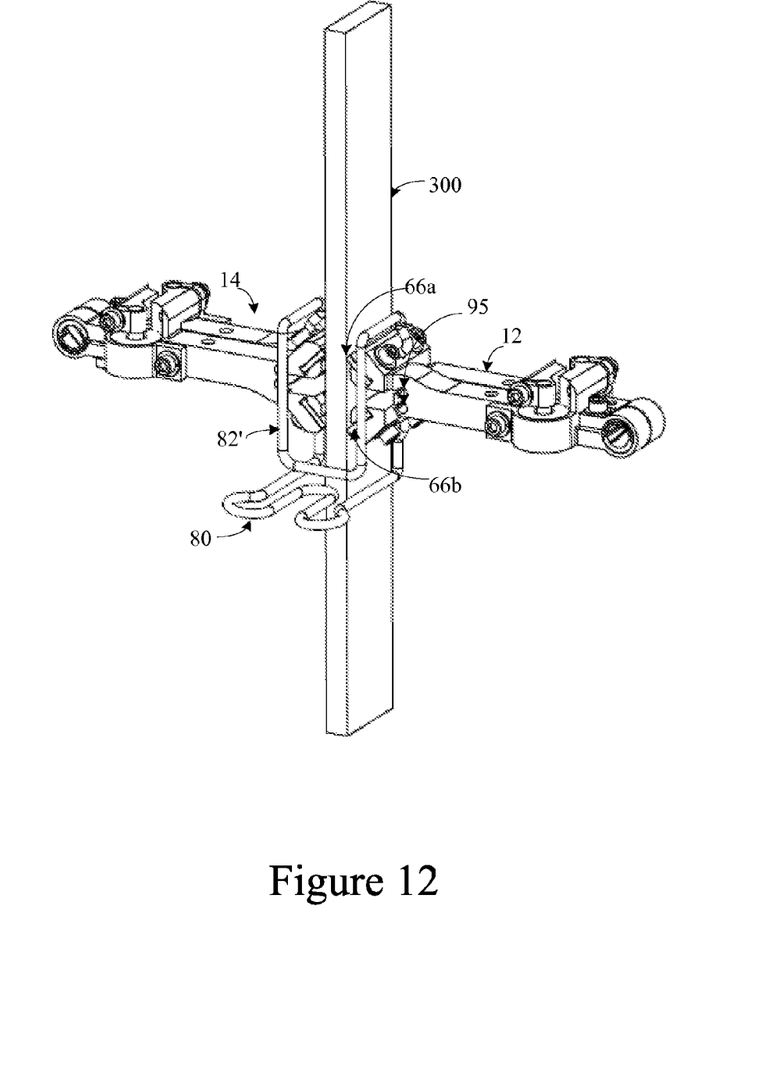
FIG. 12 of the drawings is a perspective view of a third embodiment of a pair of extensometer assemblies of the present disclosure, positioned on a specimen, which can be loaded onto a material test frame (not shown).

In yet another embodiment, shown in FIG. 12, the attachment assembly 16 is modified replacing clip 82 from the embodiment of FIGS. 9 through 11, with clip 82'. The clip 82' comprises a hoop having a plurality of bent sections such that after extending away from the extensometer arm, the first bent sections extend substantially parallel to the specimen contact member for a distance (typically to clear the side of the specimen and then extend downwardly for a distance and then loop together. The other clip 80 is substantially identical to that which is shown in the previous embodiments. It will be understood that this particular combination allows for the placement of the extensometer assembly after the specimen has been attached at both ends. In addition, the extensometer assembly can be rotated clockwise so that the specimen contact member is substantially parallel to the direction of force, with the same clips, and also after the ends of the specimen have been coupled to each other.

Additionally, and as can also be seen on the other embodiments, a plurality of holes 95 are disposed on each of the arms at strategic positions. Generally, a pin can be extended through the opening in one arm and the other arm can be pivoted until there is an opening that lines up, thereby allowing the pin to extend through the second arm, thereby locking the two arms together. While any number of specific pin locking orientations are contemplated, it is contemplated that a fully extended (i.e., the specimen contact members of each of the first and second arms are as far apart as possible to each other), fully retracted (i.e., the specimen contact members of each of the first and second arms are as close as possible to each other), and a neutral central point that is between the fully extended and the fully retracted.

The foregoing description merely explains and illustrates the invention and the invention is not limited thereto except insofar as the appended claims are so limited, as those skilled in the art who have the disclosure before them will be able to make modifications without departing from the scope of the invention.

What is claimed is:

1. An extensometer for use in association with an extensometer assembly comprising:
    a first arm having a proximal end and a distal end, and a bearing bore positioned at the proximal end thereof, with a specimen contact assembly positioned at the distal end thereof;
    a second arm having a proximal end and a distal end and a bearing bore positioned at the proximal end thereof, with a specimen contact assembly positioned at the distal end thereof;
    a flexure bearing extending between the first arm and the second arm at the proximal end of each of the first arm and the second arm and into the bearing bore positioned at the proximal ends of each of the first and second arms, so as to position the first and second arms in a side by side orientation; and
    at least one sensor assembly having a component coupled to each of the first arm and the second arm, the at least one sensor configured to sense relative pivoting of the first arm and the second arm relative to each other.

2. The extensometer of claim 1 wherein the specimen contact assembly of at least one of the first arm and the second arm comprises:
   an outer clamp component which is positioned at the distal end of the first arm;
   an inner clamp component which is configured to engage with the outer clamp component; and
   a specimen contact member configured to extend between the outer clamp component and the inner clamp component, to, in turn, sandwich the specimen contact member therebetween.

3. The extensometer of claim 2 wherein the specimen contact member extends from the distal end of the respective one of the first arm and second arm substantially perpendicular to the specimen.

4. The extensometer of claim 2 wherein the specimen contact member extends from the distal end of the respective one of the first arm and second arm substantially oblique to the specimen, and, wherein the specimen contact member comprises a generally rectangular cross-sectional configuration, to, in turn, facilitate contact with a specimen along an edge of the specimen contact member.

5. The extensometer of claim 2 wherein the flexure bearing comprises a cylindrical member which is encased within the bearing bore of each of the first arm and second arm.

6. The extensometer of claim 1 wherein the sensor subassembly further comprises a first sensor winding fixedly coupled to the first arm between the first and second end thereof, and a second sensor winding fixedly coupled to the second arm between the first and second end thereof, with a first core coupled to the second arm so as to move relative to the first sensor winding upon relative pivoting between the first arm and the second arm, and with a second core coupled to the first arm so as to move relative to the second sensor winding upon relative pivoting between the first arm and second arm.

7. The extensometer of claim 6 wherein relative pivoting movement of the first arm relative to the second arm directs one of the first core and second core further into the respective first sensor winding and second sensor winding, while at the same time directing the other of the first core and the second core further out of the respective other of the first sensor winding and second sensor winding.

8. The extensometer of claim 7 wherein the movement of the first core relative to the first winding is inversely related to the second core relative to the second winding.

9. The extensometer of claim 7 wherein the first core and the second core extends from the top surface of each of the first arm and the second arm.

10. The extensometer of claim 1 wherein each of the first arm and the second arm is formed from a single monolithic metal member.

11. The extensometer of claim 1 wherein each of the first sensor windings and the second sensor windings extend into a respective bore extending into the first arm and the second arm between the proximal and distal ends thereof.

12. The extensometer of claim 1 wherein the first sensor winding and the second sensor winding are substantially identical in configuration.

13. An extensometer assembly comprising:
    a first extensometer positionable on a first side of a specimen, and comprising a first arm and a second arm pivotally coupled to each other at a proximal end, and engageable with a specimen at a distal end thereof about a specimen contact member;
    a second extensometer positionable on a second side of a specimen, wherein a second side of a specimen is opposite the first side of a specimen, and comprising a first arm and a second arm pivotally coupled to each other at a proximal end, and engageable with a specimen at a distal end thereof about a specimen contact member; and
    an attachment assembly configured to attach the first extensometer to the second extensometer, the attachment assembly comprising:
      a first clip having a first end coupled to the distal end of the first arm of the first extensometer and a second end coupled to the distal end of the first arm of the second extensometer, wherein the first clip extends one of substantially oblique and substantially parallel to the specimen contact member, to, in turn, facilitate attachment of the extensometer assembly in an orientation wherein the specimen contact member is substantially parallel to the direction of a force that is to be applied to the specimen and in an orientation wherein the specimen contact member is substantially perpendicular to the direction of a force that is to be applied to the specimen;
      a second clip having a first end coupled to the distal end of the second arm of the first extensometer and a second end coupled to the distal end of the second arm of the second extensometer, wherein the first clip extends one of substantially oblique and substantially parallel to the specimen contact member, to, in turn, facilitate attachment of the extensometer assembly in an orientation wherein the specimen contact member is substantially parallel to the direction of a force that is to be applied to the specimen and in an orientation wherein the specimen contact member is substantially perpendicular to the direction of a force that is to be applied to the specimen.

14. The extensometer assembly of claim 13 wherein each of the first end and the second end of the first clip include a valley and the top surface of the first arm of each of the first extensometer and the second extensometer each include an opening disposed on a respective top surface thereof, wherein the respective valley of each of the first end and second end engages a respective opening of the first arm of the respective first and second extensometers, to, in turn, releasably engage the same.

15. The extensometer assembly of claim 14 wherein each of the first end and the second end of the second clip include a valley and the top surface of the second arm of each of the first extensometer and the second extensometer each include an opening disposed on a respective top surface thereof, wherein the respective valley of each of the first end and second end engages a respective opening of the first arm of the respective first and second extensometers, to, in turn, releasably engage the same.

16. The extensometer assembly of claim 14 wherein the opening disposed on the respective top surface of each of the first arms of each of the first and second extensometers is disposed at an angle that substantially corresponds to that of the valley at the first end and second end of the first clip, so that a portion of the distal end engages a surface of the opening, to, in turn, provide a surface of contact between the first and second end.

17. The extensometer assembly of claim 14 wherein each of the extensometers are tuned to a resonant frequency that is between 10 Hz and 100 Hz.

18. The extensometer assembly of claim 17 wherein each of the extensometers are tuned to a resonant frequency that is above 50 Hz.

* * * * *